(12) United States Patent
Tsai et al.

(10) Patent No.: US 7,878,336 B2
(45) Date of Patent: Feb. 1, 2011

(54) SYSTEM AND METHOD FOR INSPECTION OF CHIPS ON TRAY

(75) Inventors: Cheng Tao Tsai, Hsinchu County (TW); Chao Sheng Yu, Hsinchu County (TW)

(73) Assignee: Cheng Mei Instrument Technology Co., Ltd., Hsinchu County (TW)

( * ) Notice: Subject to any disclaimer, the term of this patent is extended or adjusted under 35 U.S.C. 154(b) by 0 days.

(21) Appl. No.: 12/555,245

(22) Filed: Sep. 8, 2009

(65) Prior Publication Data

US 2010/0063619 A1 Mar. 11, 2010

Related U.S. Application Data

(60) Provisional application No. 61/095,372, filed on Sep. 9, 2008.

(51) Int. Cl.
*B07C 5/344* (2006.01)
(52) U.S. Cl. .................. 209/552; 209/571; 209/573; 209/576; 700/213; 700/214
(58) Field of Classification Search .......... 209/552, 209/571, 573, 651, 652, 654, 903, 938; 700/213, 700/214, 275; 241/222, 226
See application file for complete search history.

(56) References Cited

U.S. PATENT DOCUMENTS

| | | | | |
|---|---|---|---|---|
| 4,907,701 A * | 3/1990 | Kobayashi et al. | .......... | 209/576 |
| 5,807,066 A * | 9/1998 | Smith | .......... | 414/802 |
| 5,906,468 A * | 5/1999 | Vander Syde et al. | ....... | 414/403 |
| 6,283,695 B1 * | 9/2001 | Nakagawa et al. | ..... | 414/416.05 |
| 6,892,740 B2 * | 5/2005 | Khoon | ..... | 134/64 R |
| 7,112,303 B2 * | 9/2006 | Itoh | .......... | 422/72 |
| 2003/0188997 A1 * | 10/2003 | Tan et al. | ..... | 209/538 |
| 2008/0224721 A1 * | 9/2008 | Kim et al. | ..... | 324/761 |
| 2010/0032262 A1 * | 2/2010 | Im et al. | ..... | 198/401 |

* cited by examiner

*Primary Examiner*—Gene Crawford
*Assistant Examiner*—Terrell H Matthews
(74) *Attorney, Agent, or Firm*—WPAT, P.C.; Anthony King

(57) ABSTRACT

A system for inspection of chips on a tray comprises an unloading arm device, a first support platform, and a plurality of first tray-handling apparatuses. The first support platform is disposed adjacent to the unloading arm device, movable along a first direction. The plurality of first tray-handling apparatuses are arrayed along the first direction on the first support platform. Each of the plurality of first tray-handling apparatuses provides a particular size of tray for inspection, different from the size of tray provided by other first tray-handling apparatuses, wherein the first platform is configured to move a desired one of the plurality of first tray handling apparatuses before the unloading arm device.

14 Claims, 9 Drawing Sheets

SYSTEM AND METHOD FOR INSPECTION OF CHIPS ON TRAY

BACKGROUND OF THE INVENTION

1. Field of the Invention

The present invention relates to a system and a method for inspection of chips, and more particularly, to a system and a method for inspection of chips on a tray.

2. Description of the Related Art

As the chip on glass (COG) packaging technique becomes more and more popular, the demand for the inspection of COG chips is quickly rising. In addition to the wafer level inspection, chips placed on a tray must be inspected before they are installed on a display panel to increase production yield or minimize the risk of repair or rework operation. In order to meet such inspection requirement, several inspection systems for inspecting chips on a tray are currently in use.

Generally, trays for receiving chips are available in sizes of 2, 3, and 4 inches. To handle this variety in tray size, complicated adjustment mechanisms have been developed for the tray-handling devices so that the tray-handling devices can be adjusted to fit the size of the trays. However, the adjustment of the tray-handling devices usually requires a significant amount time, which increases the downtime of the system. In addition, any adjustment incurs risk of damaging processing products by making an adjustment that is beyond safe limits.

An imaging sensor is usually utilized in inspection systems for detecting defects in chips on a tray. The imaging sensor is focused on the surface of a chip being inspected, and then performs the detection operation. However, in traditional inspection systems, chip detection operation is easily obstructed by the vibration caused by driving devices. The COG chips are tiny and light, and normally are loosely disposed on a tray. Therefore, vibration may cause the chips to move during inspection, resulting in difficulties in performing accurate inspection.

After inspection, defective chips are replaced with good chips in some inspection systems. In such systems, the defective chips are removed from a tray, and good chips are then placed in empty recesses on the tray. Usually, the systems use a pickup head to remove defective chips and place good chips on the tray. A single pickup head may easily become the source of cross-contamination. Moreover, the process of replacing defective chips with good chips is slow, resulting in high inspection cost.

In summary, traditional inspection systems for chips on a tray have many disadvantages, and a new inspection system without the above disadvantages is required.

SUMMARY OF THE INVENTION

One embodiment of the present invention proposes a system for inspection of chips on a tray. The system comprises an unloading arm device, a first support platform, and a plurality of first tray-handling apparatuses. The first support platform is disposed adjacent to the unloading arm device and is movable along a first direction. The plurality of first tray-handling apparatuses are disposed along the first direction on the first support platform. Each of the plurality of first tray-handling apparatuses receives a differently-sized tray for inspection, and the first support platform is configured to move a desired one of the plurality of first tray-handling apparatuses to a position in front of the unloading arm device.

The present invention proposes a method for inspection of chips on a tray. The method comprises the steps of: moving a first support platform to position a desired one of the plurality of first tray-handling apparatuses mounted on the first support platform in front of an unloading arm device to provide a tray for the unloading arm device, and each of the plurality of first tray-handling apparatuses is configured to receive trays of a certain size that is different from the size of tray received by other first tray-handling apparatus; removing a defective chip using a first pickup head from the tray; and placing a good chip onto the tray using a second pickup head.

BRIEF DESCRIPTION OF THE DRAWINGS

The invention will be described according to the appended drawings in which.

PREFERRED EMBODIMENT OF THE PRESENT INVENTION

Figure 1:
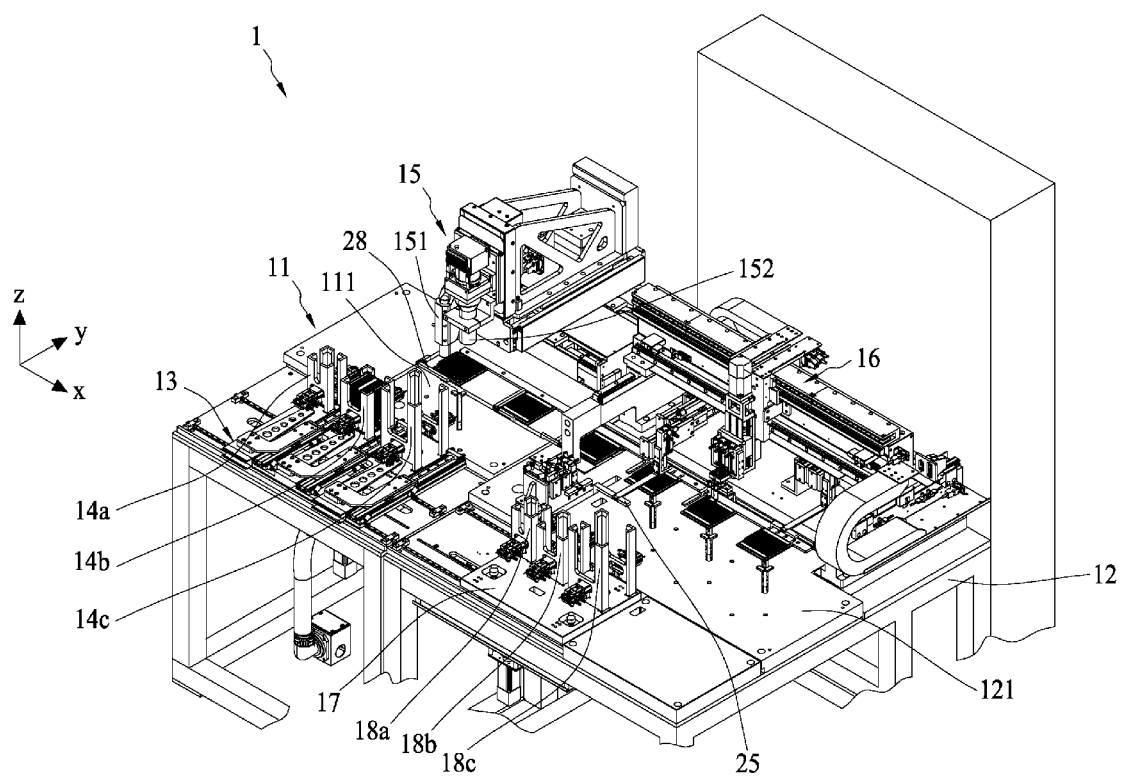
FIG. 1 is a perspective view of a system for inspection of chips on a tray according to one embodiment of the present invention.
Figure 2:
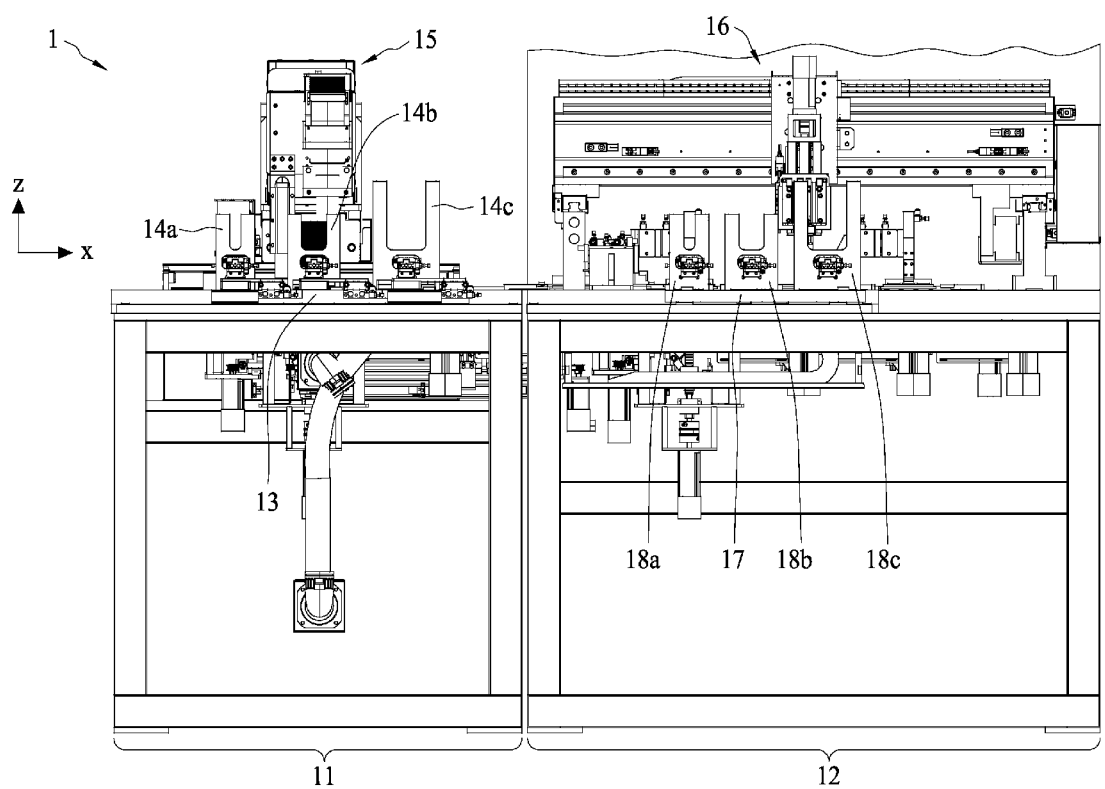
FIG. 2 is a top view showing an inspection table assembly and a support table assembly, which are separate, according to one embodiment of the present invention.
Figure 3:
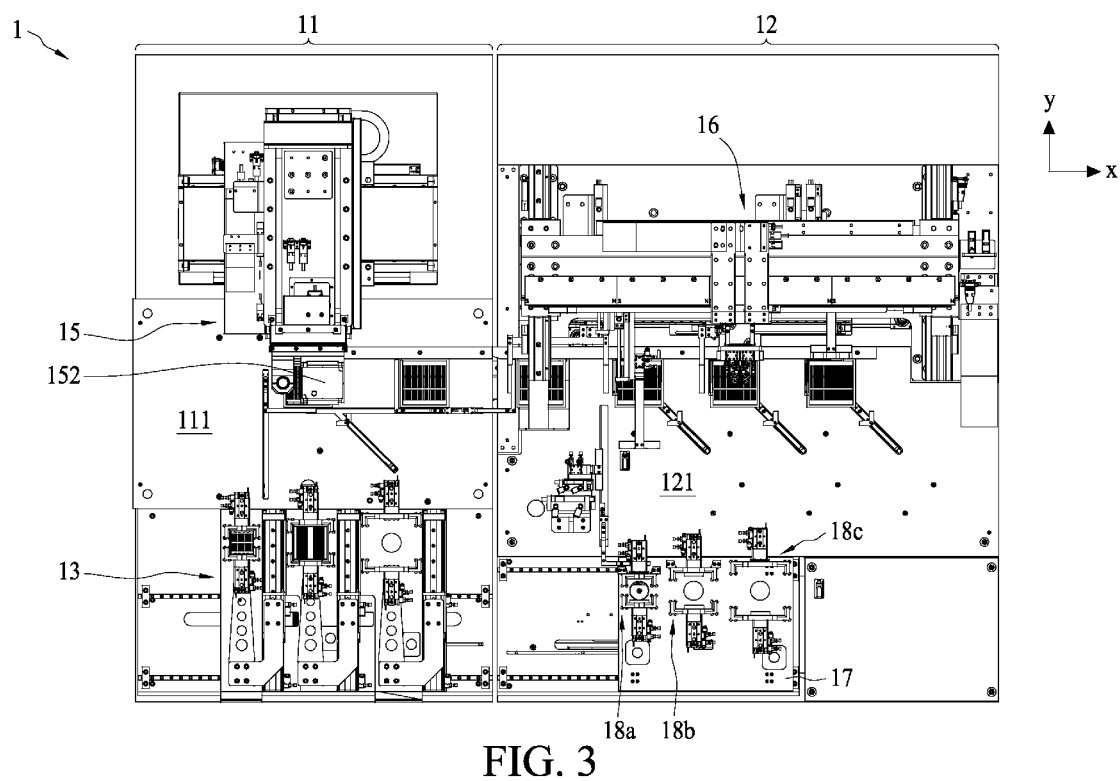
FIG. 3 is a front view of a system for inspection of chips on a tray according to one embodiment of the present invention.

Referring to FIGS. 1 to 3, the system 1 for inspection of chips on a tray comprises an inspection table assembly 11, a support table assembly 12 adjacent to the inspection table assembly 11, a first support platform 13, a plurality of first tray-handling apparatuses (14a, 14b and 14c), a chip inspection apparatus 15, a pick-and-place apparatus 16, a second support platform 17, and a plurality of second tray-handling apparatuses (18a, 18b and 18c). The first support platform 13 is disposed on the top surface of the inspection table assembly 11, adjacent to one edge of the inspection table assembly 11. The plurality of first tray-handling apparatuses (14a, 14b, and 14c) are arrayed on the first support platform 13, with their exits facing toward a first tray-supporting surface 111, on which trays are moved by pushing during inspection and chip replacement processes. The chip inspection apparatus 15 is disposed on the inspection table assembly 11, with its image sensor 152 located above the first tray-supporting surface 111. The pick-and-place apparatus 16 is disposed on the support table assembly 12, located next to the chip inspection apparatus 15, and the second support platform 17 is disposed on the support table assembly 12, adjacent to the first support platform 13. The plurality of second tray-handling apparatuses (18a, 18b and 18c) are arrayed on the second support platform 17, with their entrances facing toward a second tray-supporting surface 121. As can be better seen in FIGS. 2 and 3, the inspection table assembly 11 is disposed independently of the support table assembly 12. Thus, the inspection operation performed by the chip inspection apparatus 15 is not affected by the vibration caused by the driving devices of the pick-and-place apparatus 16 and the second tray-handling apparatuses (18a, 18b and 18c).

Figure 4:
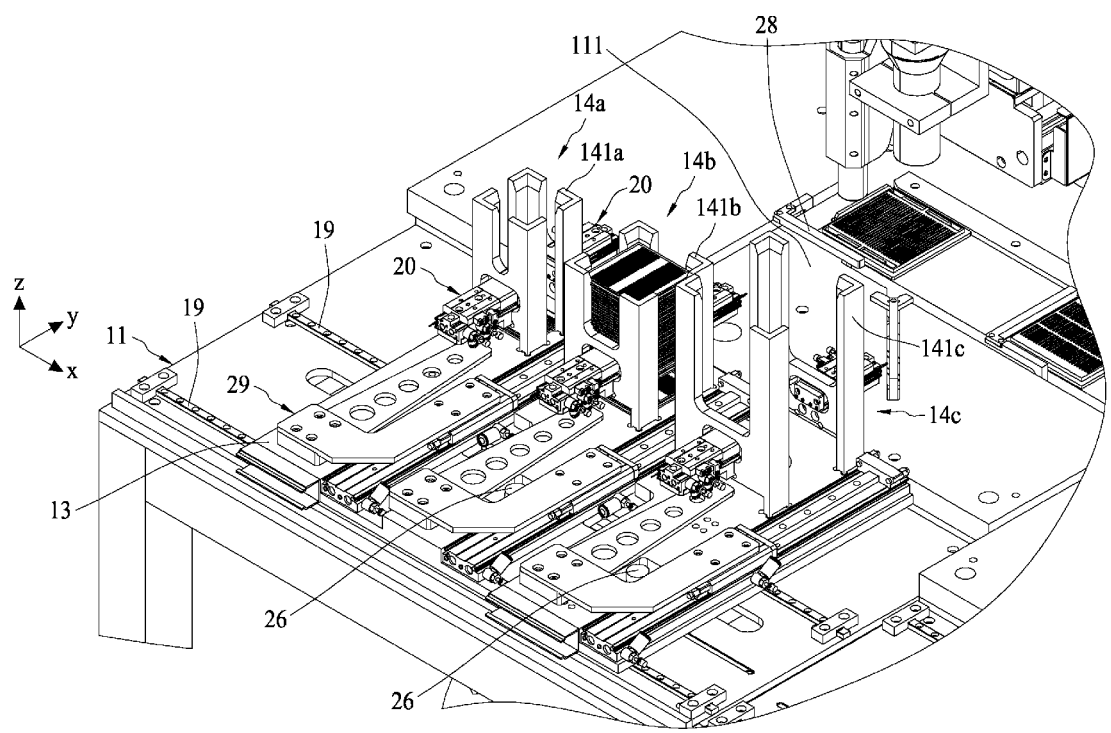
FIG. 4 is a perspective view showing a plurality of first tray-handling apparatuses mounted on a first support platform according to one embodiment of the present invention.

Referring to FIG. 4, the system 1 further comprises a plurality of guide rails 19 disposed on the inspection table assembly 11, underneath the first support platform 13, arranged lengthwise along the x-direction. The first support platform 13 is mounted on the guide rails 19 in a sliding manner so that the first support platform 13 can be, for example, manually moved along the x-direction.

A plurality of positioning pins 26 are provided to engage a plurality of openings (not shown) on the inspection table assembly 11 to immobilize the first support platform 13 after the desired first tray-handling apparatus (14a, 14b or 14c) is moved to the tray unloading position.

Specifically, the plurality of first tray-handling apparatuses (14a, 14b and 14c) are arrayed, along the x-direction, on the first support platform 13. Each of the first tray-handling apparatuses (14a, 14b and 14c) includes a stack holding portion (141a, 141b or 141c) configured for holding stacked trays. Each stack holding portion (141a, 141b or 141c) is configured to store a specific size of tray. For example, the stack holding portion 141a is configured for trays of 2 inches; the stack holding portion 141b is for trays of 3 inches; and the stack holding portion 141c is for trays of 4 inches. With the movable multiple stack holding portions (141a, 141b and 141c) designated for holding differently-sized stacked trays, the system 1 can easily handle and perform inspection on chips on differently-sized trays without any mechanical adjustment.

In the present embodiment, stacked trays are loaded to the system 1 at, but not limited to, a tray unloading position, which is in front of the unloading arm device 28 or where the first tray-handling apparatus 14b holding stacked trays in FIG. 4 is located. The first support platform 13 is located adjacent to the unloading arm device 28 and is movable along the x direction so that users can move the desired one of the size-specific first tray-handling apparatuses (14a, 14b or 14c) to a position in front of the unloading arm device 28 using the first support platform 13. The stacked trays held in the desired first tray-handling apparatus (14a, 14b or 14c) can first be moved onto the first tray-supporting surface 111 and then moved to the chip inspection apparatus 15 for inspection.

Each of the first tray-handling apparatuses (14a, 14b and 14c) comprises a pair of oppositely disposed clamping devices 20 for holding stacked trays within the respective stack holding portion (141a, 141b or 141c) and a tray loading device 29 configured to load trays onto the first tray-supporting surface 111. Each clamping device 20 can include a linear motor for its driving source. Stacked trays in each of the first tray-handling apparatuses (14a, 14b and 14c) can be moved vertically by a linear motion device such as pneumatic cylinder or linear motor.

Figure 5:
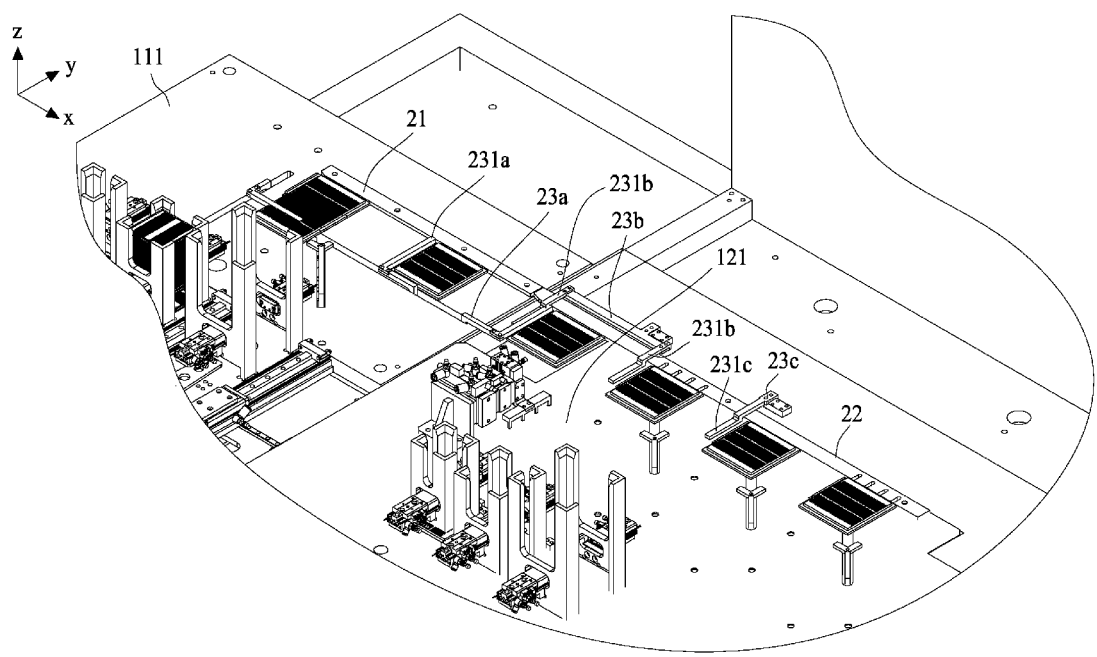
FIG. 5 is a perspective view showing first and second elongated guide strips according to one embodiment of the present invention.

Referring primarily to FIG. 5, but also referring to FIG. 1, the system 1 further comprises a first elongated guide strip 21 and a second elongated guide strip 22. The first elongated guide strip 21 is disposed on the first tray-supporting surface 111, before the chip inspection apparatus 15 as shown in FIG. 1; the second elongated guide strip 22 is disposed on the second tray-supporting surface 121, before the pick-and-place apparatus 16 as shown in FIG. 1. The first elongated guide strip 21 and the second elongated guide strip 22 are configured to guide moving trays being processed and are aligned along the x-direction.

Referring to FIG. 5 again, processing trays are pushed and moved on the first tray-supporting surface 111 and the second tray-supporting surface 121. It can be seen that the roughness of the first tray-supporting surface 111 and the second tray-supporting surface 121 should be small, usually 5 micrometers or less. In addition, the first tray-supporting surface 111 and the second tray-supporting surface 121 can be properly leveled to each other so that trays can be moved smoothly from the first tray-supporting surface 111 to the second tray-supporting surface 121. Further, each of a plurality of tray-moving mechanisms (23a, 23b and 23c) includes a push bar (231a, 231b and 231c) transversely disposed relative to and moving in the direction along the first elongated guide strip 21 and the second elongated guide strip 22 for pushing inspecting trays.

Figure 6:
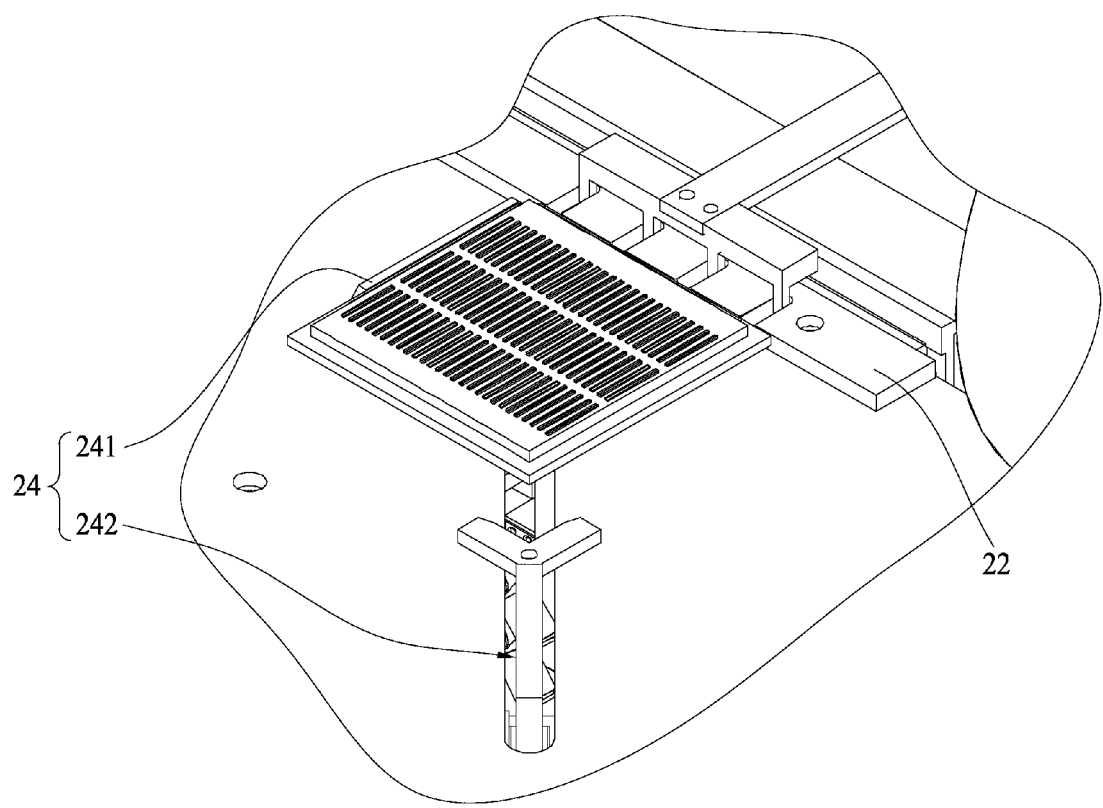
FIG. 6 is a perspective view showing a positioning mechanism according to one embodiment of the present invention.

Referring to FIG. 6, the system 1 further comprises a plurality of positioning mechanisms 24 disposed along the first elongated guide strip 21 and second elongated guide strip 22 and configured for positioning trays before chip inspection or pick-and-place process as shown in FIG. 5. Each positioning mechanism 24 includes a datum bar 241 for defining a datum position for trays and a positioning arm device 242 having a V-shaped head. Each datum bar 241, transverse relative to the first elongated guide strip 21 and the second elongated guide strip 22, is normally under the first tray-supporting surface 111 and the second tray-supporting surface 121, and in the path along which trays are moved. The V-shaped head 2421 of each positioning arm device 242 is adapted to move linearly toward and away from a corner surrounded by the respective datum bar 241 and the first elongated guide strip 21 or the second elongated guide strip 22, with the V-shaped recess facing the same corner. When a tray is prepared for positioning, the datum bar 241 moves upward, rising above the first tray-supporting surface 111 or above the second tray-supporting surface 121 and then the V-shaped head 2421 of the positioning arm device 242 moves to engage a corner of the tray, pushing the tray against the datum bar 241 and the first elongated guide strip 21 or against the datum bar 241 and the second elongated guide strip 22.

Figure 7:
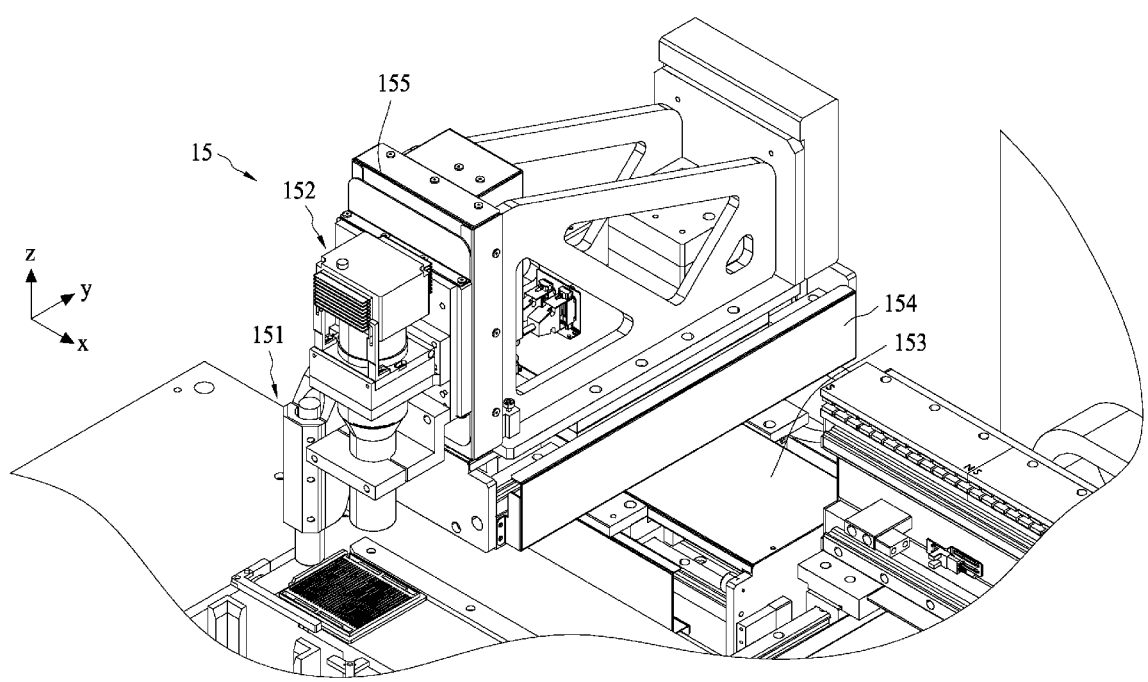
FIG. 7 is a perspective view showing a chip inspection apparatus according to one embodiment of the present invention.

Referring to FIG. 7, chips on trays are inspected using the chip inspection apparatus 15. The chip inspection apparatus 15 may include a focus device 151 for determining the focus positions of chips on trays and an image device 152 for obtaining the images of the chips on trays according to their focus positions to determine defective chips. Both the focus device 151 and the image device 152 can be moved along the x, y and z directions using, but not limited to, an X stage 153, a Y stage 154, and a Z stage 155 as shown in FIG. 7.

Figure 8:
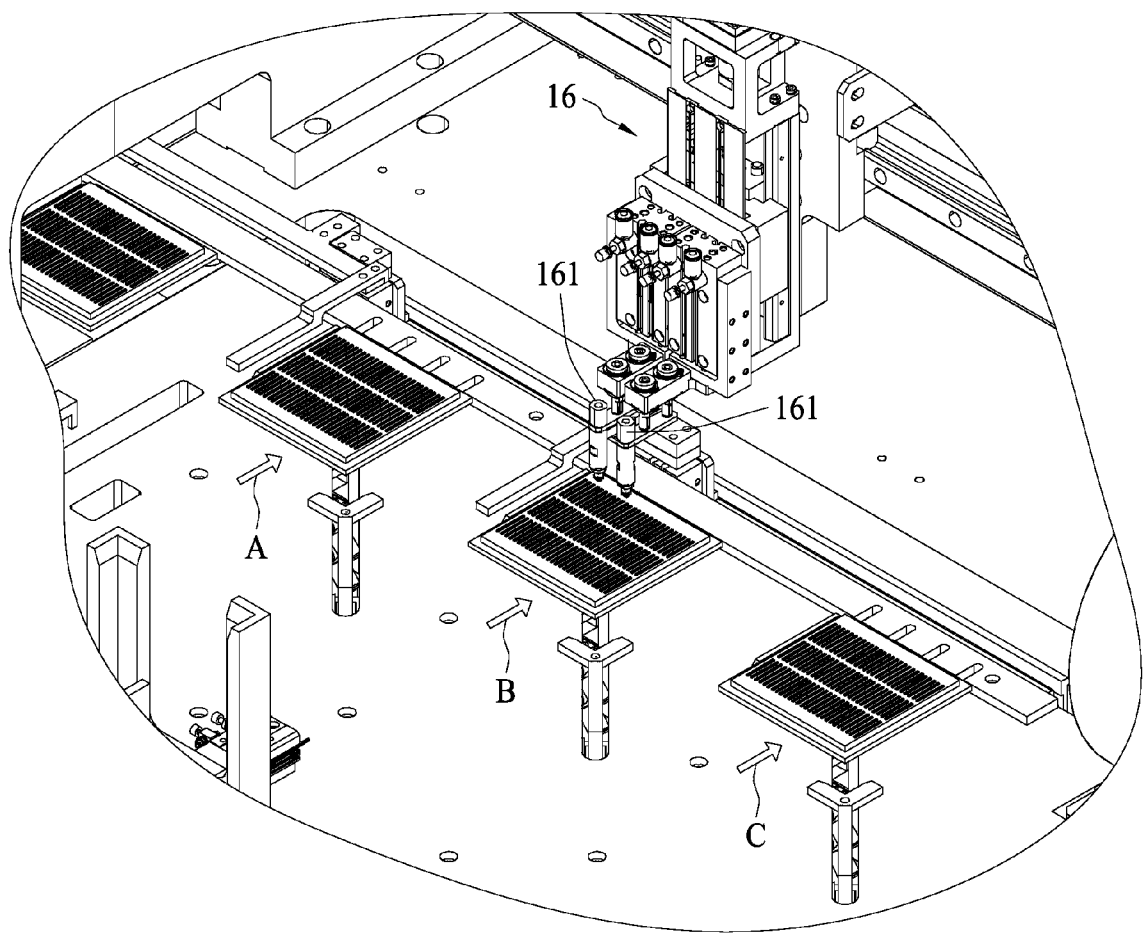
FIG. 8 is a perspective view showing a pick-and-place apparatus according to one embodiment of the present invention.

Referring to FIG. 8, the pick-and-place apparatus 16 includes a pair of pickup heads 161. One of the pickup heads 161 is used for removing defective chips from the inspected tray at the position indicated by arrow A to the tray at the position indicated by arrow C and another of the pickup heads 161 is used for moving a good chip from the tray at the reservation area indicated by arrow B to the inspected tray at the position indicated by arrow A for replenishing the vacancies of the inspected tray left due to the removal of defective chips. The pickup heads 161 can move independently from each other, each being driven by a pneumatic cylinder or motor. The pair of pickup heads can be simultaneously moved using an XYZ stage, or moved by other means. The step of removing a defective chip and the step of moving a good chip to an inspected tray can be performed in an alternating manner. Defective chips and good chips are moved using different pickup heads 161 so that there is no risk of causing cross contamination.

Figure 9:
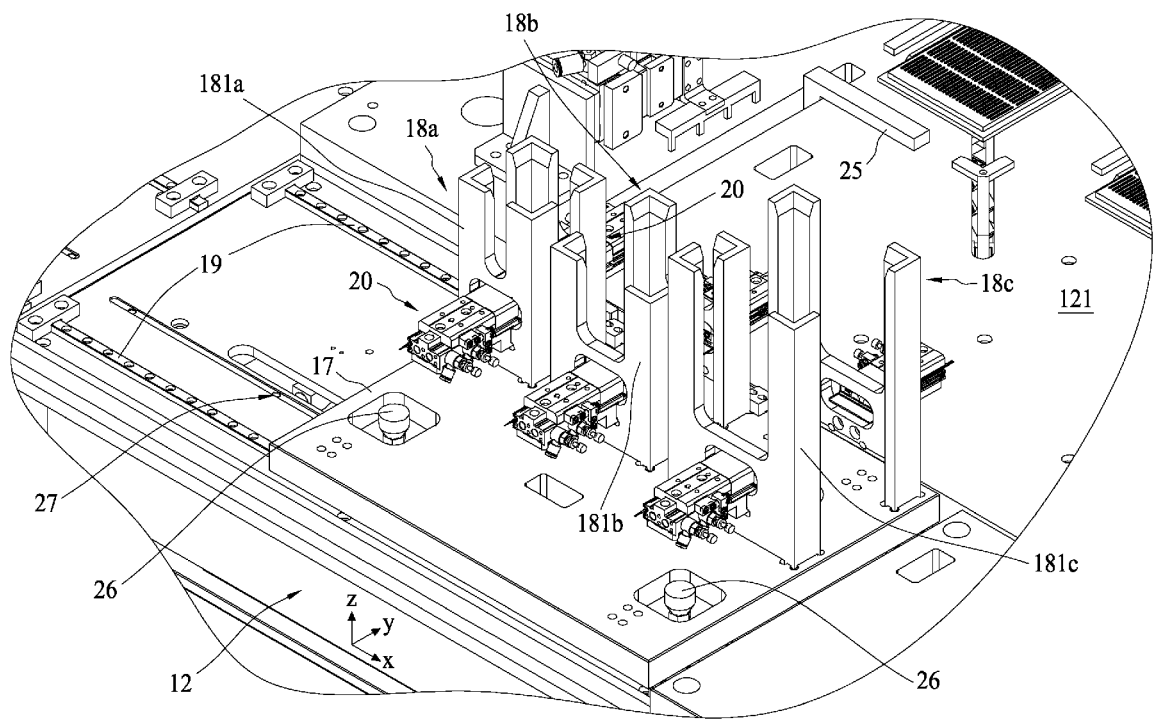
FIG. 9 is a perspective view showing a plurality of second tray-handling apparatuses mounted on a second support platform according to one embodiment of the present invention.

Referring to FIG. 9, a plurality of second tray-handling apparatuses (18a, 18b and 18c), arrayed along the x-direction or other direction, and mounted on the second support platform 17 with entrances facing the second tray supporting surface 121, are provided for receiving inspected trays of different sizes provided by the respective first tray-handling apparatuses (14a, 14b and 14c). A plurality of guide rails 19 are disposed on the support table assembly 12, underneath the second support platform 17, arranged lengthwise along the x-direction. The second support platform 17 is mounted on the guide rails 19 in a sliding manner so that the second support platform 17 can be manually moved along the x-direction.

A plurality of positioning pins 26 are provided to secure the second support platform 17 by engaging openings 27 provided on the support table assembly 12 after the desired second tray-handling apparatus (18a, 18b or 18c) is moved to the tray loading position.

Each of the plurality of second tray-handling apparatuses (18a, 18b and 18c) is moved to a tray loading position, in front of and in the path of the movement of the loading arm device 25, using the second support platform 17 before it starts to receive inspected trays. Each of the second tray-handling apparatuses (18a, 18b and 18c) also comprises a pair of oppositely disposed clamping devices 20 for holding stacked trays within the respective stack holding portion (181a, 181b or 181c), each receiving differently sized trays. Stacked trays in each of the second tray-handling apparatuses (18a, 18b and 18c) can be moved vertically by a linear motion device such as a hydraulic cylinder or linear motor.

The present invention provides a method for inspection of chips on a tray. The method initially moves a first support platform to position a desired one of the plurality of first tray-handling apparatuses arrayed on the first support platform in front of an unloading arm device. The first support platform is movable along a first direction. The plurality of first tray-handling apparatuses are arrayed on the first support platform along the first direction, and each of the plurality of first tray-handling apparatuses provides a differently-sized tray for inspection.

Next, a second support platform is moved to position a desired one of the plurality of second tray-handling apparatuses arrayed on the second support platform in front of a loading arm device so that inspected trays can be moved into the desired one of the plurality of second tray-handling apparatuses using the loading arm device, wherein each of the plurality of second tray-handling apparatuses is configured to receive the trays of the particular size provided by its corresponding first tray-handling apparatus. The second support platform is movable along a second direction. In the present embodiment, the first direction is the same as the second direction. The plurality of second tray-handling apparatuses are arrayed on the second support platform along the second direction.

Next, a tray is moved from the first tray-handling apparatus located in front of the unloading arm device to a chip inspection apparatus for chip inspection. Thereafter, defective chips are removed from an inspected tray and good chips are provided to the inspected tray in replacement of the defective chips using a pick-and-place apparatus. The pick-and-place apparatus include a pair of pickup heads. One of the pickup heads of the pick-and-place apparatus is configured for removal of defective chips and another of the pickup heads is configured for provision of good chips. In the present embodiment, a good chip is initially picked by one pickup head, and a defective chip is then removed from a chip holding recess of the inspected tray by anther pickup head, and finally the picked good chip is placed in the chip holding recess of the inspected tray from which the defective chip was just removed. The above steps can be performed in an alternating manner until all defective chips are removed. Such a process can largely increase the throughput of the system. The tray providing good chips can be one of the inspected trays, located on a reservation area, and if the tray providing good chips has no good chips, a newly inspected tray will be moved to the reservation area to replace it.

Finally, the inspected tray loaded with good chips is moved to the desired one of the plurality of second tray-handling apparatuses, positioned before a loading arm device.

The above-described embodiments of the present invention are intended to be illustrative only. Numerous alternative embodiments may be devised by persons skilled in the art without departing from the scope of the following claims.

What is claimed is:

1. A system for inspection of chips on a tray, comprising:
an unloading arm device;
a first support platform disposed adjacent to the unloading arm device and movable along a first direction;
a plurality of first tray-handling apparatuses disposed along the first direction on the first support platform, each receiving a differently-sized tray for inspection, wherein the first support platform is configured to move a desired one of the plurality of first tray-handling apparatuses to a position in front of the unloading arm device to allow the unloading arm device to move trays from the desired first tray-handling apparatus;
a loading arm device;
a second support platform disposed adjacent to the loading arm device and movable along a second direction; and
a plurality of second tray-handling apparatuses arrayed along the second direction on the second support platform, each of the plurality of second tray-handling apparatuses configured to receive the trays of the particular size provided by its corresponding first tray-handling apparatus, wherein the second support platform is configured to move a desired one of the plurality of second tray-handling apparatuses to a position in front of the loading arm device to allow the loading arm device to move an inspected tray to the desired second tray-handling apparatus.

2. The system of claim 1, further comprising a pick-and-place apparatus including a pair of pickup heads, wherein one of the pickup heads of the pick-and-place apparatus is configured for removal of a defective chip from the inspected tray and another of the pickup heads is configured for provision of a good chip to the inspected tray.

3. The system of claim 2, further comprising a chip inspection apparatus, a support table assembly and an inspection table assembly disposed independently of the support table assembly, wherein the chip inspection apparatus and the first support platform are disposed on the inspection table assembly, and the pick-and-place apparatus and the second support platform are disposed on the support table assembly.

4. The system of claim 3, wherein each of the first support platform and the support second platform comprises a positioning pin, and each of the inspection table assembly and the support table assembly comprises a plurality of openings for engaging the respective positioning pin.

5. The system of claim 3, further comprising a first guide rail disposed underneath the first support platform and a second guide rail disposed underneath the second support platform, wherein the first support platform is mounted on the first guide rail in a sliding manner and the second support platform is mounted on the second guide rail in a sliding manner.

6. The system of claim 3, wherein the chip inspection apparatus includes a focus device for determining the focus positions of chips and an image device for obtaining the images of the chips according to the focus positions to determine defective chips.

7. The system of claim 3, further comprising a plurality of elongated guide strips separately disposed on the inspection table assembly and the support table assembly, wherein inspecting trays are guided by the plurality of guide strips when the inspecting trays are moving.

8. The system of claim 7, further comprising a plurality of positioning mechanisms disposed along the plurality of the guide strips, each positioning mechanism comprising a datum bar and a positioning arm device, wherein each datum bar is disposed transversely relative to the plurality of the guide strips and the positioning arm device is configured to move toward and away from an included corner surrounded by the datum bar and the respective one of the plurality of the guide strips.

9. The system of claim 3, wherein the inspection table assembly comprises a first tray supporting surface configured to allow the processing tray to move smoothly and the support table assembly comprises a second tray supporting surface configured to allow the processing tray to move smoothly, wherein the first tray supporting surface is properly leveled to the second tray supporting surface.

10. A method for inspection of chips on a tray, comprising steps of:
  moving a first support platform to position a desired one of the plurality of first tray-handling apparatuses arrayed on the first support platform in front of an unloading arm device to provide a tray for the unloading arm device, wherein each of the plurality of first tray-handling apparatuses is configured to receive the tray with different size;
  removing a defective chip using a first pickup head from the tray;
  placing a good chip onto the tray using a second pickup head; and
  moving a second support platform to position a desired one of the plurality of second tray-handling apparatuses arrayed on the second support platform in front of a loading arm device to receive an inspected tray using the loading arm device, wherein each of the plurality of second tray-handling apparatuses is configured to receive the trays of the particular size provided by its corresponding first tray-handling apparatus.

11. The method of claim 10, further comprising a step of moving the tray to a chip inspection apparatus using the unloading arm device.

12. The method of claim 10, wherein the step of removing a defective chip and the step of placing a good chip are performed in an alternating manner.

13. The method of claim 10, wherein the step of placing a good chip comprises steps of:
  picking the good chip by the second pickup head before the step of removing a defective chip; and
  placing the good chip into a location of the defective chip following the step of removing a defective chip.

14. The method of claim 10, further comprising a step of moving an inspected tray to a reservation area for providing the good chip.

* * * * *